United States Patent
Mitsuyama et al.

(10) Patent No.: US 9,476,893 B2
(45) Date of Patent: *Oct. 25, 2016

(54) AUTOMATIC ANALYSIS DEVICE AND ANALYSIS METHOD

(75) Inventors: Satoshi Mitsuyama, Tokyo (JP); Chihiro Manri, Kawagoe (JP); Tomonori Mimura, Kasama (JP); Kumiko Kamihara, Mito (JP)

(73) Assignee: Hitachi High-Technologies Corporation, Tokyo (JP)

(*) Notice: Subject to any disclaimer, the term of this patent is extended or adjusted under 35 U.S.C. 154(b) by 1293 days.

This patent is subject to a terminal disclaimer.

(21) Appl. No.: 13/321,072

(22) PCT Filed: May 10, 2010

(86) PCT No.: PCT/JP2010/003150
§ 371 (c)(1),
(2), (4) Date: Nov. 17, 2011

(87) PCT Pub. No.: WO2010/134277
PCT Pub. Date: Nov. 25, 2010

(65) Prior Publication Data
US 2012/0064636 A1    Mar. 15, 2012

(30) Foreign Application Priority Data
May 20, 2009   (JP) .................. 2009-121531

(51) Int. Cl.
*G01N 35/00*    (2006.01)

(52) U.S. Cl.
CPC .. *G01N 35/00663* (2013.01); *G01N 35/00623* (2013.01); *G01N 2035/0097* (2013.01); *G01N 2035/00702* (2013.01)

(58) Field of Classification Search
CPC ............................................. G01N 2035/00702
See application file for complete search history.

(56) References Cited

U.S. PATENT DOCUMENTS

2009/0222213 A1*   9/2009   Hamazumi et al. ............ 702/19

FOREIGN PATENT DOCUMENTS

| JP | 57-147039 A | 9/1982 |
| JP | 2004-347385 A | 12/2004 |
| JP | 2006-337125 A | 12/2006 |
| JP | 2007-248089 A | 9/2007 |
| JP | 2009-204448 A | 9/2009 |
| JP | 2010-261822 A | 11/2010 |
| JP | 2010-271095 A | 12/2010 |

* cited by examiner

*Primary Examiner* — P. Kathryn Wright
(74) *Attorney, Agent, or Firm* — Mattingly & Malur, PC

(57) ABSTRACT

Provided are an automated analyzer and an automatic analysis method for highly accurately determining presence or absence of abnormality based on reaction process data obtained when concentration of a chemical component or an activity level of an enzyme is measured. The reaction process data is approximated by a function, and shape feature quantities indicating features of a shape of a curve section at an early stage of reaction are calculated. The obtained shape feature quantities are used to determine the presence or absence of abnormality.

18 Claims, 14 Drawing Sheets

AUTOMATIC ANALYSIS DEVICE AND ANALYSIS METHOD

TECHNICAL FIELD

The present invention relates to an automated analyzer that performs qualitative or quantitative analysis of a biological sample, such as blood and urine, and particularly, to an automated analyzer and an analysis method with a function of monitoring reaction of an analyzer for clinical examination.

BACKGROUND ART

An automated analyzer for clinical examination dispenses certain amounts of a sample and a reagent to stir and react the sample and the reagent. The automated analyzer measures absorbance of a reaction solution throughout a certain time and calculates a concentration, an activity value, and the like of a measurement target substance based on a measurement result.

Reagents for each analysis item, a standard solution for calibrating the reagents, an quality control sample that is measured to check the states of the analyzer and the reagents in the analysis, and the like are necessary in addition to the analyzer in the analysis for clinical examination. The materials other than the analyzer are combined to obtain ultimate analysis performance.

Examples of factors inside the analyzer that directly affect the analysis performance include a sampling mechanism, a reagent dispensing mechanism, a stirring mechanism, an optical system, a reaction container, and a thermostatic bath. Examples of factors other than the automated analyzer, include acidity or alkalinity of a reagent, a sample, and a control specimen.

To use the automated analyzer on a daily basis, the factors need to be checked to determine whether the clinical examination can be normally performed. The factors are checked, for example, as follows.

(1) Calibration Using Standard Solution Calibration is carried out for each reagent bottle of each item. A blank solution and a standard solution are measured, an origin is determined, an absorbance per unit concentration is calculated, and a conversion factor (hereinafter, abbreviated as "K-factor"), is calculated. In general, the clinical technologist checks the magnitude of the absorbance and a chronological change in the K-factor to determine the quality of the calibration result.

(2) Quality Control

A quality control sample with a known concentration is measured after the calibration to check the difference from a reference value. In the measurement of a patient specimen, the quality control sample is periodically measured every certain time to check the difference from a tolerance. If the tolerance is exceeded, it is determined that there is a problem in one of the reagent and the analyzer, and inspection is performed.

The absorbance is measured for a plurality of times during the reaction of the sample and the reagent, and the absorbance is recorded as time-series data. The time-series data is also called reaction process data. The data in daily examinations are checked based on the reaction process data. The method varies depending on the analysis method. The measurement method of clinical examination can be classified into two types, a rate method and an endpoint method, depending on the analysis method.

The rate method is mainly used to measure the activity of enzyme components included in the sample, and an activity value of the enzyme, not the concentration of the enzyme, is measured. In the measurement method, a certain amount of substrate is added as the reagent. The enzyme consumes the substrate, and a changed element is measured. If the concentration of the substrate is high to some extent, the enzyme reaction speed approaches a theoretical upper limit. The reagent of biochemical item measurement includes enough substrate. Therefore, if the sample and the reagent normally react, the measurement value of the reaction usually linearly changes by certain amounts relative to the time change.

Conventional detection methods of data abnormality during measurement in the rate method include linearity check and ABS limit. In the linearity check, the linearity of the absorbance change is checked for an analysis item of the rate method. A difference between amounts of absorbance change in the first half and the second half in a certain photometry period is obtained, and it is determined that the change does not indicate linearity if the difference is beyond a designated linearity check value. If the concentration or the enzyme activity value of the measured sample is abnormally high and is beyond the measurable range of the reagent, the substrate or the coenzyme in the reagent is all consumed before the end of photometry period. In such cases, the absorbance value rapidly changes, and a correct measurement value cannot be obtained. Therefore, a reaction absorbance limit value (ABS limit) for the upper limit or lower limit of the absorbance is set to detect the abnormality of the data.

The concentration of components, such as protein and fat, included in the sample are mainly measured by the endpoint method. Since the substance generated by the reaction of the components in the sample and the reagent approaches a certain amount with time, the measurement value also approaches the certain value with time.

An example of a conventional detection method of data abnormality during the measurement in the endpoint method includes prozone check. In a reagent using turbidimetric immunoassay, such as IgA (immunoglobulin A) and CRP (C reactive protein), protein may be deposited as a sediment due to the influence of salt concentration of the reagent composition. The sediment may fluctuate the reaction process data, and the fluctuation actually occurs at the second half section of the reaction time in many cases. If the fluctuation occurs in photometry time points used for the concentration calculation, the concentration value cannot be accurately obtained. Examples of the method for checking the fluctuation include an antibody re-addition method and a ratio of reaction rate method, which are methods of issuing an alarm when a designated limit value is exceeded in a parameter.

Examples of methods of using the reaction process data to determine the presence or absence of abnormality include known methods disclosed in Patent Literatures 1 and 2. In the method of Patent Literature 1, a chemical reaction model is used in advance, reference time-series data is generated and stored, reaction process data of a sample is compared with the reference time-series data, and it is determined that there is an abnormality if the deviation is large. In the method of Patent Literature 2, an absorbance change is approximated by a function stored in advance, and the abnormality is determined from the magnitude of the deviation between the absorbance change calculated by an approximated function and the actually measured absorbance.

CITATION LIST

Patent Literature
Patent Literature 1: JP 2004-347385 A
Patent Literature 2: JP 2006-337125 A

SUMMARY OF INVENTION

Technical Problem

In recent years, various items can be highly accurately analyzed using a small amount of sample or reagent due to the improvement in the performance of the automated analyzer. On the other hand, accurate analysis may not be possible due to a tiny abnormality of components of the analyzer, a small change in the property of the sample or the reagent, or the like. The automated analyzer for clinical examination measures, at certain intervals, the absorbance of the solution used for the reaction of the sample and the reagent and measures the absorbance change ratio and the ultimate absorbance based on the time-series absorbance. The concentration and the activity value of the enzyme are calculated from the data. In the process of the reaction, the automated analyzer carries out sampling, reagent dispensing, and stirring, and a plurality of error factors are included in the process. Particularly, the presence/absence or the level of stirring cannot be quantitatively evaluated in the past, and there is no criteria. The evaluations of the quality of reproducibility, the presence or absence of defective measurement (measurement values indicating that a problem may have occurred, such as discontinuous measurement values), and the like are vague. For a factor that directly affects the reaction, such as dilution of the reagent by wash water of a reagent probe and wrong mixing of another solution with the reagent by the user, the automated analyzer needs to detect the abnormality and prompt the user for a re-examination or maintenance of the analyzer.

It is difficult for the examination technologist as a user of the automated analyzer to visually check the entire reaction process in daily examination operations. Particularly, if the measurement value is within a normal value range, the technologist tends to overlook the reaction abnormality and an inaccurate result may be output.

Patent Literature 1 discloses the following formula as a chemical reaction model. In the formula, t denotes time, x denotes absorbance, and A0, A1, and K are parameters.

$$x = A0 + A1 \exp(-Kt) \quad (1)$$

Other than Expression (1), Patent Literature 2 discloses the following formulas as functions for approximating the absorbance change. In the formulas, t denotes time, x denotes absorbance, and A, B, and K are parameters.

$$x = -Kt + B \quad (2)$$

$$x = A/(1+Kt) + B \quad (3)$$

In the rate method, the absorbance changes in a curved manner relative to the time in a very early stage of the reaction, and the change in the absorbance becomes linear with a lapse of time. In Expressions (1) and (3), a reaction process, in which the reaction rapidly progresses as in the endpoint method and enters a steady state, can be accurately approximated. On the other hand, in a reaction process in which the reaction linearly progresses as in the rate method, the reaction does not end within about ten minutes of observation, and the absorbance continues to linearly increase or decrease until the substrate is consumed, there is a problem that the accuracy of approximation is low and it is difficult to distinguish a difference of change in reactivity. It is difficult in Expression (2) to approximate the curve section at an early stage of reaction in the rate method, and it is difficult to detect abnormality that affects the shape of the curve section.

For example, FIGS. 2 and 3 show results of approximating the reaction process data of the examination item measured by the rate method based on the formula shown in Expression (1). FIG. 2 shows normal reaction process data, and FIG. 3 shows reaction process data when a stir abnormality is artificially generated. A horizontal axis 110 denotes a lapse of time, and a vertical axis 120 denotes absorbance. Markers 130 denote actually measured absorbance, and a curve 140 denotes an absorbance change approximated by Expression (1). It can be recognized from FIGS. 2 and 3 that an error of the approximation formula from the absorbance data at the first point is large. In the example, the approximation error for the normal data is greater than the approximation error for the stir abnormality data. Therefore, it is difficult to detect abnormality by the conventional method in which the abnormality is detected based on the magnitude of an error of the approximation formula.

In the endpoint method, the measurement value is calculated from the difference between the absorbance values before the reaction and after the reaction, and the reaction speed hardly depends on the concentration of the sample. However, the activity value of the enzyme is converted from the amount of absorbance change per minute in the rate method, and the measurement value and the reaction speed change at a certain rate. Therefore, although it is sufficiently possible to evaluate the analyzer's performance by comparing the parameters of the sample with constant concentration, such as the standard substance for accuracy control. However, it is difficult to evaluate the data of a patient sample whose measurement results are not constant and concentration is unknown.

Solution to Problem

The problems can be solved by calculating an index indicating features of a change until the time-series data of the measurement values measured with a lapse of time approaches a straight line in the measurement of the concentration or the activity level of the measurement target substance included in the sample and determining the presence or absence of the abnormality based on the index.

The problems can be solved by approximating the time-series data of the measurement values measured with a lapse of time by a function with parameters that approach the straight line in the measurement of the concentration or the activity level of the measurement target substance included in the sample, using the function to calculate an index indicating shape features of the absorbance change until approaching the straight line, and determining the presence or absence of the abnormality based on the values of the index or the parameters.

The problems can be solved by approximating the time-series data of the measurement values measured with a lapse of time by a function with parameters in the measurement of the concentration or the activity level of the measurement target substance included in the sample, obtaining a tangent at the time when a second time derivative of the function is minimum, calculating an index indicating shape features of an absorbance change until the function approaches the tangent, and determining the presence or absence of the abnormality based on the values of the index or the parameters.

The problems can be solved by approximating the time-series data of the measurement values measured with a lapse of time by a function expressed by x=ax+b+h(t, φ), where t denotes time of measurement of the measurement value, x denotes the measurement value, a and b are parameters, and h (t, φ) is a function that includes a plurality of parameters φ and that approaches 0, in the measurement of the concentration or the activity level of the measurement target substance included in the sample and determining the presence or absence of abnormality based on the values of the parameters a, b, and φ.

More specifically, the present invention includes the following.

(1) An automated analyzer including: a reaction container; first dispense means for dispensing a sample to the reaction container; second dispense means for dispensing a reagent to be reacted with the sample dispensed to the reaction container; stir means for mixing the sample and the reagent in the reaction container; a measurement unit that acquires a plurality of measurement point data in a reaction process of the sample and the reagent; a data processing unit that processes the measurement point data; a storage unit that stores a function used in the data processing unit; and an output unit that outputs a processing result of the data processing unit, wherein the data processing unit selects one of a plurality of approximation formulas stored in the storage unit to approximate the plurality of measurement point data and uses an index obtained from an approximated curve to determine abnormality of measurement.

(2) The automated analyzer according to (1), wherein the control unit calculates parameters of the approximation formula to reduce a square error between the measurement data and the approximated curve to set the index.

(3) The automated analyzer according to (1), wherein the approximation formulas stored in the storage unit are set for each combination of the examination item and the reagent.

(4) The automated analyzer according to (1), wherein the approximation formula is one of the following Expressions (4) to (7).

$$x=a*t+b+c*\exp(-k*t) \qquad (4)$$

$$x=a*t+b+e/(t+d) \qquad (5)$$

$$x=a*t+b+w/\{\exp(u*t)+v\} \qquad (6)$$

$$x=a*t+b+p*\log\{1+q*\exp(r*t)\} \qquad (7)$$

(5) The automated analyzer according to (1), wherein in an approximated curve in which the plurality of measurement point data are approximated, at least one of the shape feature quantities 1. to 4. is used as the index to determine abnormality, wherein a tangent of the approximated curve at the start of reaction is a first straight line, and a straight line that is approached by the approximated curve is a second straight line.

1. A time when the first and second straight lines intersect.
2. A time when the second straight line is approached below a predetermined threshold.
3. A difference between values of the first and second straight lines at a reaction start time.
4. A difference between slopes of the first and second straight lines.

(6) The automated analyzer according to (5), wherein the storage unit includes distribution data of shape feature quantities obtained from the reaction process data in a normal state and shape feature quantities obtained from reaction process data in an abnormal state, and the shape feature quantities calculated from the measurement data are applied to determine abnormality.

(7) The automated analyzer according to (5), wherein the storage unit includes data with combinations of types of abnormalities and determination formulas using the shape feature quantities, and the data processing unit determines an abnormality type.

(8) The automated analyzer according to (6), wherein the type of abnormality is one of a stirring abnormality of the stir means, a dispense abnormality of the dispense means, and an abnormality of the reagent.

(9) The automated analyzer according to (1), wherein the abnormality is determined at preset time intervals from the start of the reaction.

(10) The automated analyzer according to (1), wherein the storage unit includes an index and shape feature quantities of the plurality of measured data, and the abnormality is determined by selecting data of a specific condition among the plurality of measured data.

(11) The automated analyzer according to (1), wherein the storage unit includes an index and shape feature quantities of the plurality of measured data, and the abnormality is determined based on a distribution of the index and the shape feature quantities of the plurality of measured data.

(12) The automated analyzer according to (1), wherein a tangent at a time when an absolute value of a second time derivative of the approximated curve is minimum is obtained, the tangent is used to calculate an index of the approximated curve, and the abnormality is determined based on the index.

(13) The automated analyzer according to (12), wherein a function expressed by $$x=ax+b+h(t,\phi)$$

is used as the approximation formula for time-series data of measurement values measured with a lapse of time, in which t denotes time when the measurement value is measured, x denotes the measurement value, a and b denote parameters, and h (t, φ) denotes a function that includes a plurality of parameters φ and that approaches 0, and the parameters a, b, and φ are set as the index to determine abnormality.

(14) The automated analyzer according to (1), wherein the measurement unit includes a light source for directing light to the reaction container and a detection unit that detects light transmitted through the reaction container.

(15) An analysis method using a measurement unit that acquires measurement point data in a reaction process of a sample and a reagent, a data processing unit that processes the measurement point data, and a storage unit that stores a function used in the data processing unit, wherein the measurement unit acquires a plurality of measurement point data in the reaction process of the sample and the reagent, and the data processing unit selects one of a plurality of approximation formulas stored in the storage unit to approximate the plurality of measurement point data and uses an index obtained from an approximated curve to determine abnormality of measurement.

FIG. 4 is a diagram schematically showing an absorbance change of a reaction solution in generally used rate analysis based on a two-liquid system. The horizontal axis 110 denotes a lapse of time, and the vertical axis 120 denotes absorbance. A curve 150 denotes a change in the absorbance. The sample in the reaction container is first mixed with a first reagent (time t0). The mixed solution is then incubated at an appropriate temperature. In the meantime, a side reaction or the like that does not affect the measured wavelength progresses, a second reagent is added and stirred at a time t1 at the end of the side reaction, the main reaction is started, and the absorbance of the measured wavelength changes in an increasing or decreasing direction. Although the main reaction starts from the time t1, the speed of the reaction is not necessarily constant from the beginning, and the speed is substantially constant after a certain time (time t2 in FIG. 4) (the reaction enters a steady state, and the change in the absorbance indicates a straight line). The time from t1 to t2, which is a time from the start of the reaction to the constancy of the speed, is generally called a lag time.

The lag time varies depending on the measurement item, the composition of the reagent, the condition of stirring, the reaction temperature, and the concentration of the specimen. For example, the lag time of γGT (γ glutamyltransferase), LD (lactate dehydrogenase), or the like is large, while the lag time of ALP (alkaline phosphatase), AST (aspartate aminotransferase), or the like is small. This is because the lag time varies depending on the difference in the activity of the enzyme, the condition of stirring, and the like. In this way, since the lag time is largely derived from the reactivity of the sample and the reagent, the reactivity of the item can be evaluated by quantifying the time until the lag time enters a steady reaction or quantifying the degree of the curve.

The present invention uses an approximation formula obtained from reaction process data to provide, continuously and for each single examination, an index that can check the analyzer abnormality, the degradation in the reagent, and the quality control. Parameters for evaluating the time or the size of the lag time in the reaction process of each measurement result, the degree of deviation from the straight line, and the like are numerically expressed by obtaining the approximation formula according to the present invention. Since the obtained parameters depend on the reagent or the item, the numeric values are used as an index to evaluate whether the reaction has progressed in an optimal state. Examples of the reaction process data to be used include not only the absorbance data and the like, and values and the like that can be measured in the reaction process may also be used.

ADVANTAGEOUS EFFECTS OF INVENTION

The use of the evaluation method of the present invention allows evaluating not only the control and the standard solution, but also each measurement result of patient specimen with unknown concentration. If the evaluation of the measurement of each specimen is possible, the reliability of the measurement data can be guaranteed based on the data of the control. For a factor in which the abnormality of the analyzer affects the reaction process data, the abnormality can be checked from daily examination data, and this can contribute to the maintenance of the performance of the analyzer.

As for the influence of stirring, if, for example, the stirring stops, the reaction speed changes, and the curve of the reaction process data also changes. The calculation and monitoring of the change in the reaction process curve in a specimen with known concentration, such as a control specimen and a standard solution, leads to checking of the chronological performance of the stirring mechanism. The automated analyzer can actively notify the analyzer user of the necessity of the maintenance and the replacement of the stirring mechanism. The presence or absence or the level of stirring, for which the evaluation has been vague, can be quantified, and as for the lag time, the reaction process immediately after the stirring after the addition of the second reagent is monitored. As a result, an optimal condition of stirring can be set. Therefore, not only the abnormality of the stirring mechanism can be detected, but also optimal parameters of each item and each reagent can be verified and determined.

If a reagent is degraded or diluted by wash water in the reagent probe, the reaction speed is affected. According to the present invention, the inactive degree of the reaction can be numerically expressed, and the reaction abnormality can be detected. The reagent performance can be evaluated, the degradation in the reagent by a human error in the daily examination can be detected, and the overlook of output of wrong data can be prevented.

DESCRIPTION OF EMBODIMENTS

First Embodiment

Figure 5:
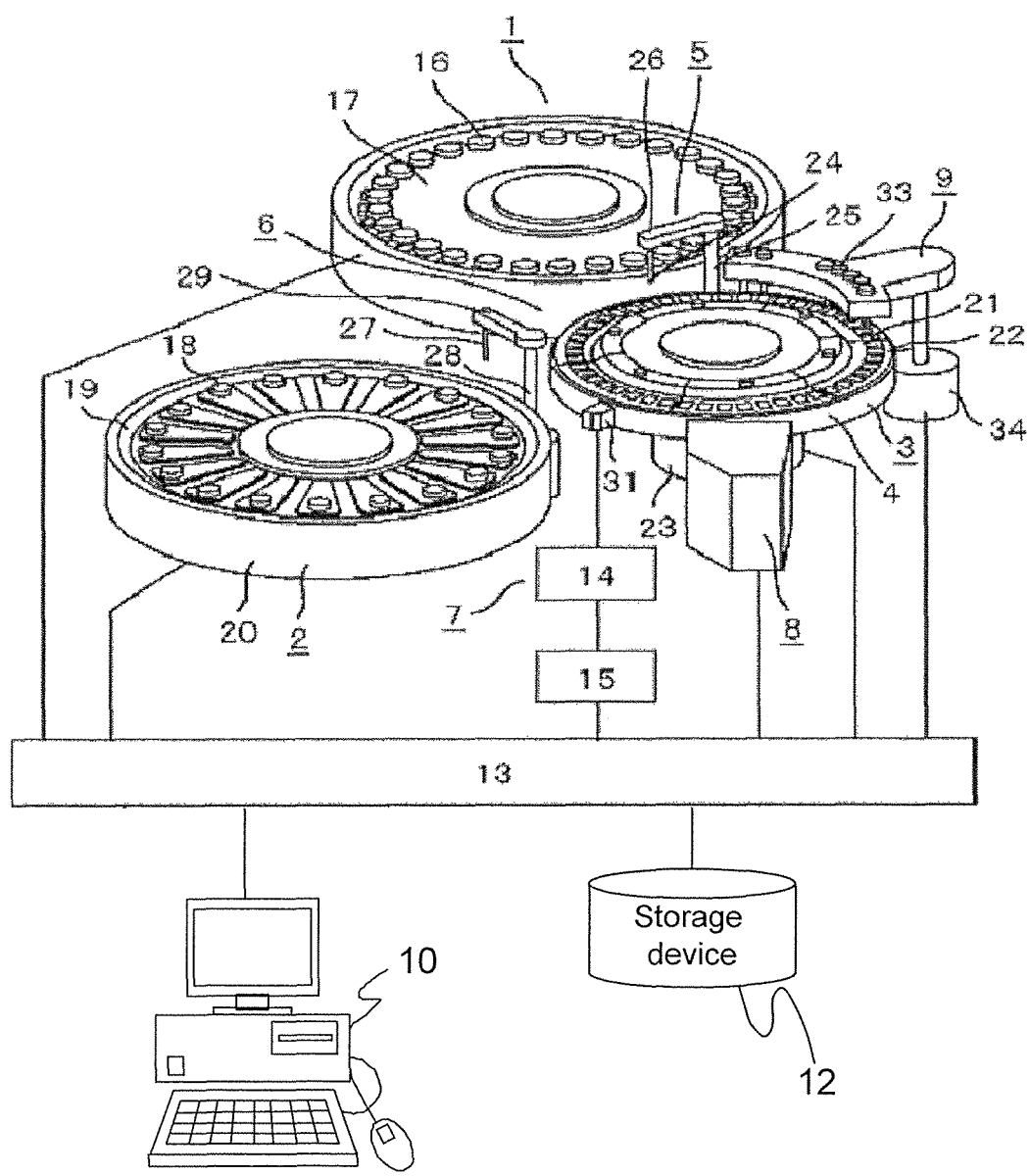
FIG. 5 is a diagram showing a schematic configuration of an automated analyzer to which the present invention is applied.

Hereinafter, a first embodiment of the present invention will be described in detail with reference to the drawings. FIG. 5 is a diagram showing a schematic configuration of a biochemical automated analyzer to which the present invention is applied. Reference numeral 1 denotes a sample disc, 2 denotes a reagent disc, 3 denotes a reaction disc, 4 denotes a reaction vessel, 5 denotes a sampling mechanism, 6 denotes a pipetting mechanism, 7 denotes a stirring mechanism, 8 denotes a photometric mechanism, 9 denotes a washing mechanism, 10 denotes a computer (PC), 12 denotes a storage device, 13 denotes a control unit, 14 denotes a piezoelectric element driver, 15 denotes a stirring mechanism controller, 16 denotes sample containers, 17 and 19 denote circular discs, 18 denotes a reagent bottle, 20 denotes a cooling box, 21 denotes a reaction container, 22 denotes a reaction container holder, 23 denotes a drive mechanism, 24 and 27 denote probes, 25 and 28 denote support shafts, 26 and 29 denote arms, 31 denotes a fixation unit, 33 denotes a nozzle, and 34 denotes a vertical drive mechanism. The storage device 12 stores analysis parameters, possible numbers of times of analysis of reagent bottles, maximum possible numbers of times of analysis, calibration results, analysis results, and the like. As described below, a sample is analyzed in the order of sampling, reagent dispensing, stirring, photometry, washing of the reaction container, and data processing such as concentration conversion.

The control unit 13 controls the sample disc 1 through the computer 10. A plurality of sample containers 16 are circumferentially aligned and set on the sample disc 1, and the sample containers 16 move to below the sampling probe 24 according to the order of analyzed samples. As for the specimen in the sample containers 16, a predetermined amount of specimen is dispensed inside the reaction container 21 by a pump for sample connected to the specimen sampling mechanism 5.

The reaction container 21 provided with the sample moves inside the reaction vessel 4 up to a first reagent addition position. A pump for reagent (not shown) connected to the reagent dispense probe 6 adds a predetermined amount of reagent sucked from the reagent container 18 to the moved reaction container 21. The reaction container 21 after the addition of the first reagent moves to the position of the stirring mechanism 7, and first stirring is performed. The addition of reagent and the stiffing is performed for, for example, first to fourth reagents.

The reaction container 21, in which the content is stirred, passes through a luminous flux generated from a light source, and the photometric mechanism 8 of a multi-wavelength photometer detects the absorbance at this time. The detected absorbance signal enters the control unit 13 and is converted to a concentration of the specimen. At the same time, the control unit 13 determines the abnormality based on the absorbance.

The data converted to the concentration is stored in the storage device 12 and displayed on a display device attached to the computer 10. The reaction container 21 after photometry is finished moves to the position of the washing mechanism 9, and the reaction container 21 is washed and provided to the next analysis.

Figure 1:
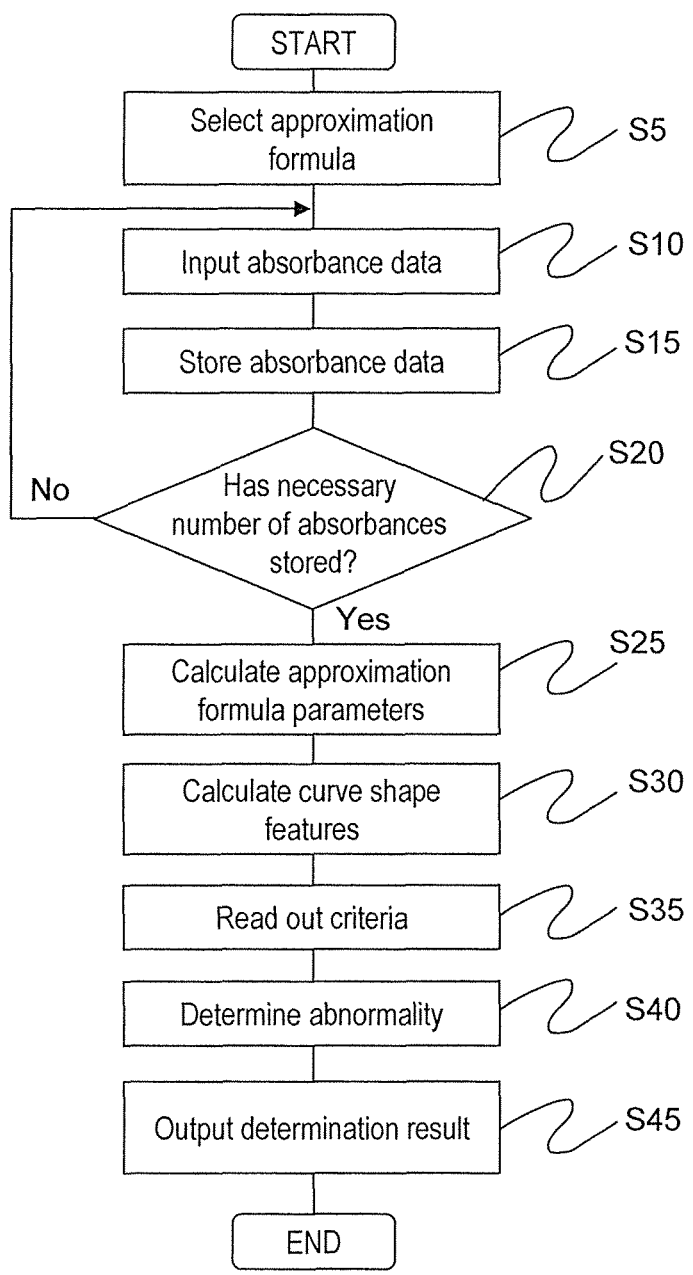
FIG. 1 is a diagram showing a processing flow of a first embodiment of the present invention.
Figure 14:
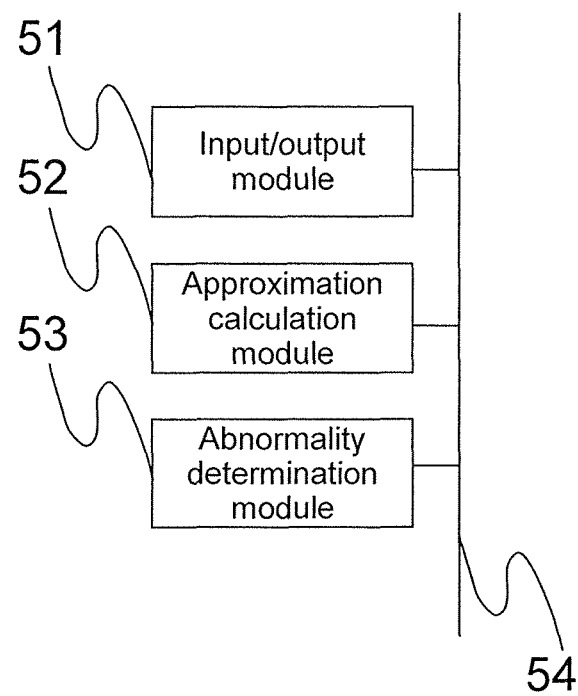
FIG. 14 is a diagram showing an example of configuration in a control unit 13.

Next, details of a process by the control unit 13 determining abnormality based on the absorbance will be described with reference to FIG. 1. FIG. 1 is a diagram showing a processing step of the part related to the abnormality determination in the control unit 13. FIG. 14 is a diagram showing an example of configuration of the part of executing the process shown in FIG. 1 in the control unit 13. An input/output module 51, an approximation calculation module 52, and an abnormality determination module 53 are connected to each other through a data bus 54, and the modules can mutually transfer data. The input/output module 51 transfers data with the photometry mechanism 8, the computer (PC) 10, and the storage device 12. The modules may be included as separate hardware or CPU, or the modules may be included as software modules within the same CPU.

First, measurement of an examination item of a specimen is started, and at the same time, the approximation calculation module 52 selects and reads out an optimal approximation formula corresponding to the combination of the examination item and the reagent among a plurality of approximation formulas indicating the time change of the absorbance stored in the storage device 12 through the input/output module 51 in step S5. The selection can be automatically determined based on the combination of the examination item and the reagent. For example, functions shown in Expression (4) to Expression (7) are stored in advance in the storage device 12 as the approximation formulas. In the formulas, t denotes time, and x denotes absorbance. Furthermore, a, b, c, d, e, k, p, q, r, u, v, and w are parameters. The optimal approximation formula of each combination of the examination item and the reagent may be stored in a table, and the table may be used to select the optimal approximation formula corresponding to the combination of the examination item and the reagent.

$$x=a*t+b+c*\exp(-k*t) \tag{4}$$

$$x=a*t+b+e/(t+d) \tag{5}$$

$$x=a*t+b+w/\{\exp(u*t)+v\} \tag{6}$$

$$x=a*t+b+p*\log\{1+q*\exp(r*t)\} \tag{7}$$

Figure 9:
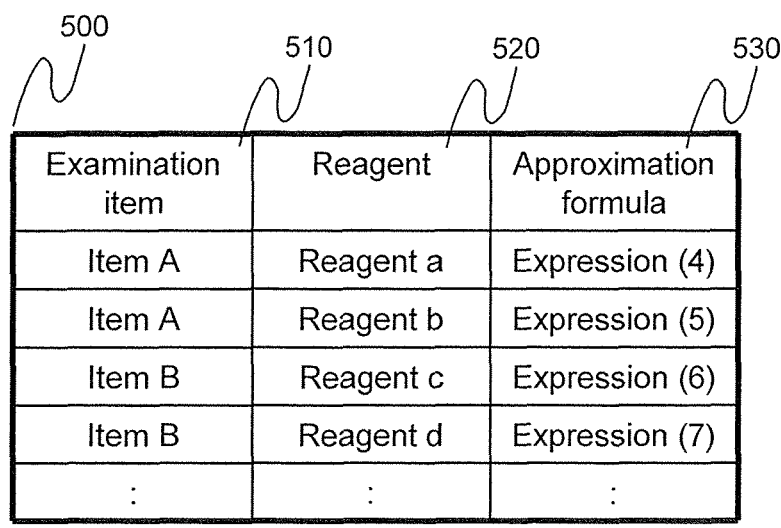
FIG. 9 is a diagram showing an example of a table describing types of optimal approximation formulas for combinations of the types of examination items and reagents.

For example, a table 500 describing optimal approximation formulas are stored in advance in the storage device 12 for the combinations of the examination items and the reagents to be used as shown in FIG. 9. A column 510 describes the examination items, and a column 520 describes the types of the reagents. A column 530 describes the types of optimal approximation formulas for the examination items and the types of the reagents. Based on the combinations of the examination items and the reagents, the table 500 is used in step S5 to select the optimal approximation formula. The user may be able to change the content of the table.

The absorbance is measured for a plurality of times with a lapse of time, and the input/output module 51 inputs absorbance data of one measurement or an average of a plurality of times of measurements to the control unit 13 including calculation means from the photometry mechanism 8 in step S10. In a measurement system using two-wavelength light including light of a wavelength (main wavelength) in which the absorbance significantly changes with a change in the color tone associated with the reaction of the reagent and the specimen as well as light of a wavelength (sub wavelength) in which the absorbance hardly changes, the difference between the absorbance of the main-wavelength light and the absorbance of the sub-wavelength light is input as absorbance data. In step S15, the input/output module 51 stores the input absorbance data in the storage device 12. In step S20, the input/output module 51 determines whether absorbance data necessary in the following process is stored. If the necessary data is not stored, the process returns to S10, and the input and the storage of the absorbance data are repeated until the necessary number of data is stored. If the necessary number of data is stored, the process moves to step S25.

In step S25, the approximation calculation module 52 calculates the values of the parameters in the formula so that the difference between the time change of the absorbance expressed by the approximation formula selected in step S5 and the time change of the actual absorbance becomes as small as possible. Specifically, the parameter values in the formula are determined so that the square error between the measured and stored absorbance data and the absorbance calculated by the approximation formula becomes as small as possible. Although an existing least squares calculation method can be used to calculate the parameter values, an example of a method that can handle formulas in various forms includes a steepest descent method, and the parameter values that minimize the square error are calculated. In a reaction using a plurality of reagents, a large change of the absorbance starts after the addition of a reagent (last reagent in general) that causes a main absorbance change. In this case, only the data after the addition of the reagent that causes the main absorbance change is used for the calculation of the parameter values.

Figure 2:
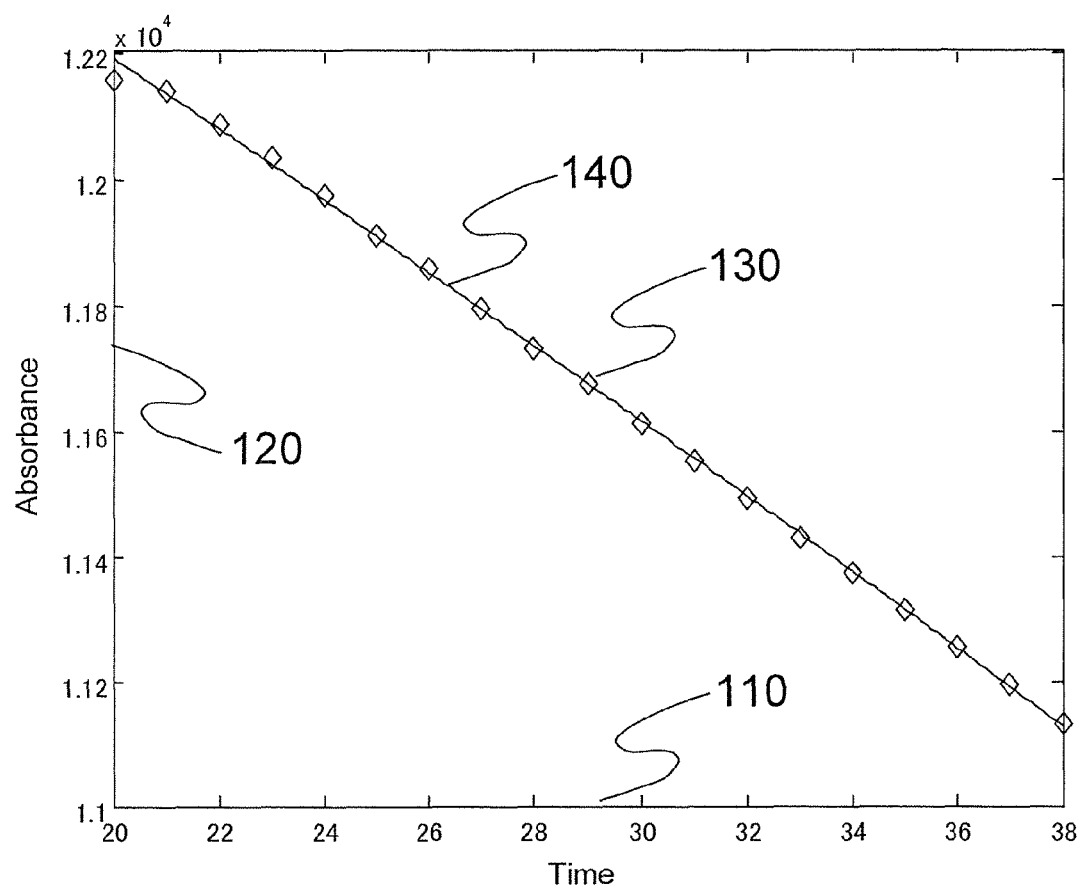
FIG. 2 is a diagram showing an example in which normal reaction process data is approximated by a function based on Expression (1).
Figure 3:
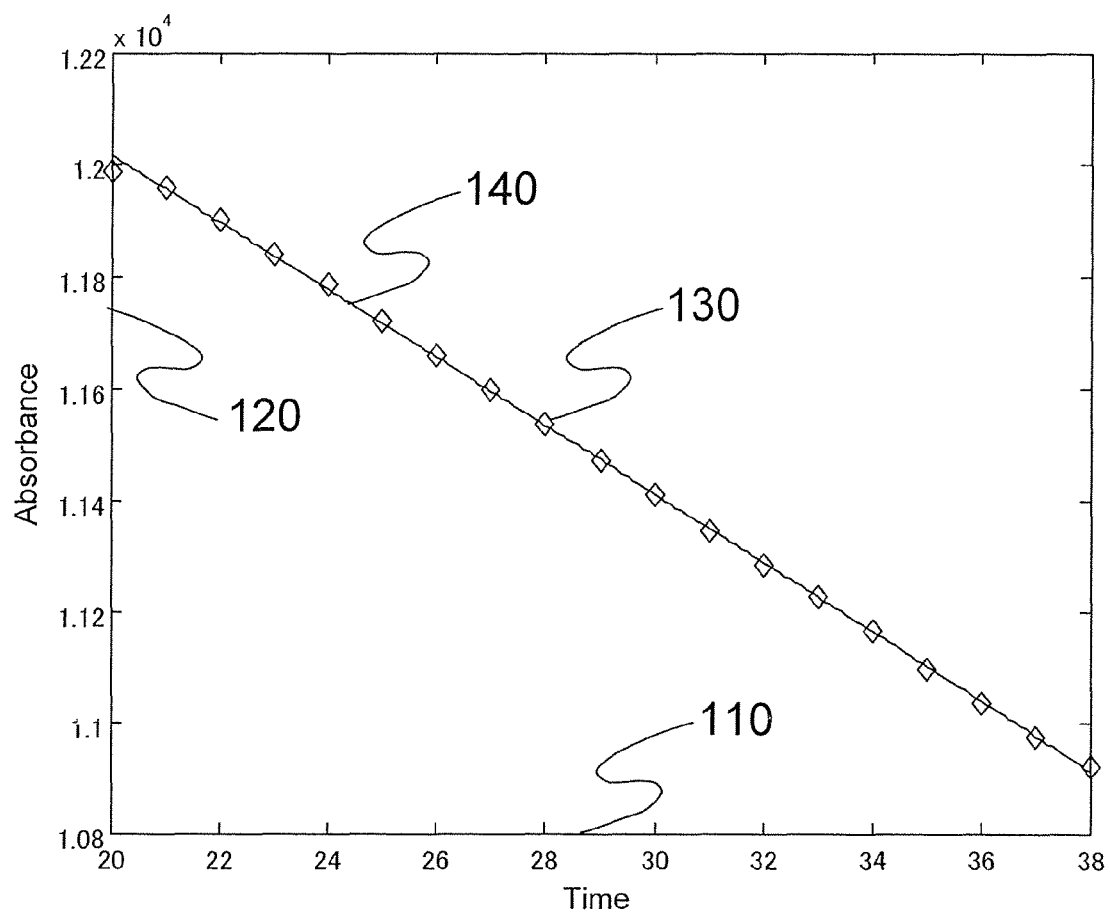
FIG. 3 is a diagram showing an example in which abnormal reaction process data is approximated by a function based on Expression (1).
Figure 4:
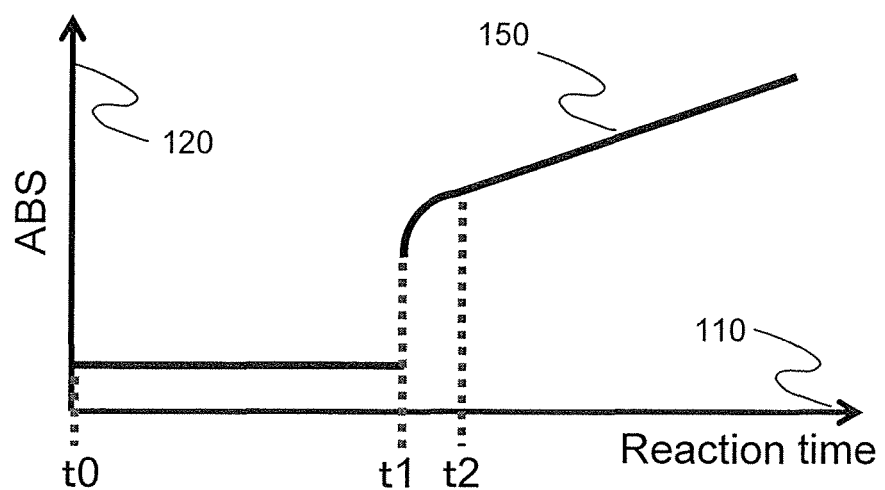
FIG. 4 is a diagram showing schematic of reaction process data of a rate method.
Figure 6:
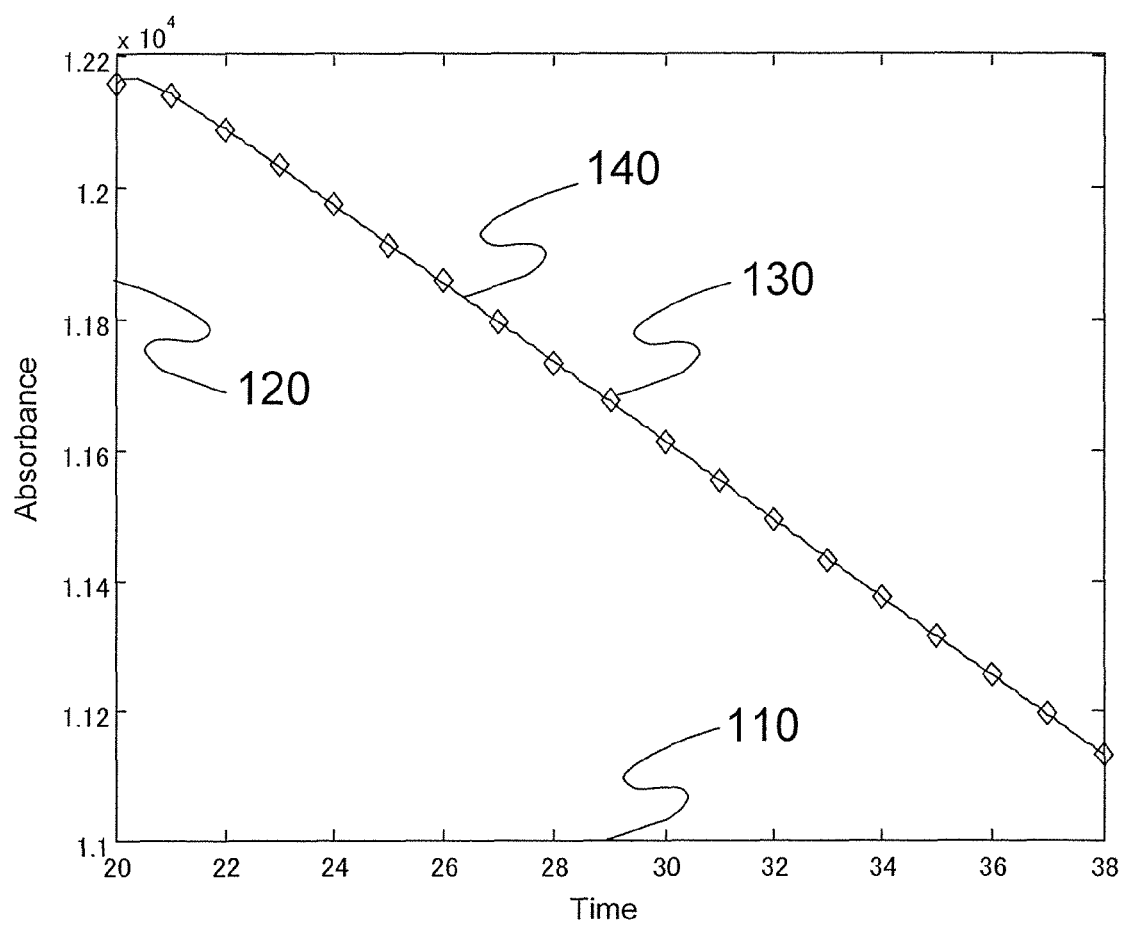
FIG. 6 is a diagram showing an example in which reaction process data is approximated by a function according to the present invention.

To detect abnormality in the present invention, the difference between the absorbance calculated by the approximate formula and the actually measured absorbance needs to be sufficiently small for normal data in step S25. The approximation formula according to the conventional technique has a problem that the accuracy of the approximation of the curve section is poor at an early stage of the reaction as shown in FIGS. 2 and 3. However, the curve section at an early stage can also be accurately approximated using Expression (4) to Expression (7). FIG. 6 shows a result of approximating the same data as the reaction process data shown in FIG. 2 using, for example, Expression (5). Compared to FIG. 2, it can be recognized that the accuracy of approximation for the absorbance data at the first point is improved.

Figure 7:
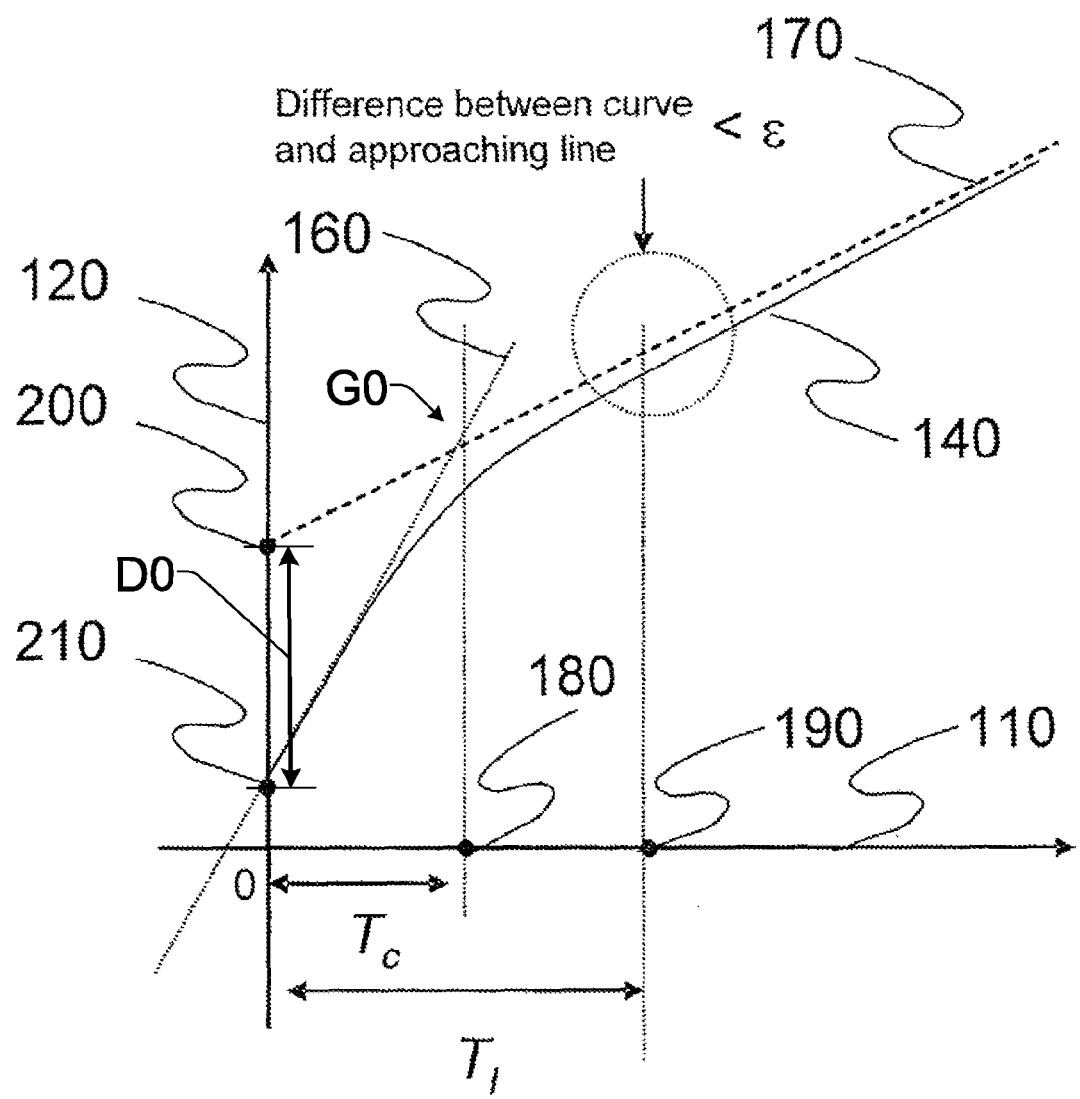
FIG. 7 is a diagram explaining a method of numerically expressing shape features of a curve section at an early stage of reaction.

Next, in step S30, the approximation calculation module 52 calculates numeric values (shape feature quantities) indicating features of an absorbance change pattern of the part where the absorbance at an early stage of reaction changes in a curved matter. An example of the shape feature quantities will be described with reference to FIG. 7. In FIG. 7, the horizontal axis 110 denotes a lapse of time from the start of the reaction, and the vertical axis 120 denotes absorbance. The curve 140 denotes an approximated curve of the absorbance change calculated by the approximation formula. A straight line 160 denotes a tangent of the curve 140 at the start of the reaction, and a straight line 170 denotes a straight line approached by the curve 140. A point 180 on the horizontal axis 110 denotes time that the straight line 160 and the straight line 170 intersect. A point 190 on the horizontal axis 110 denotes time that the curve 140 sufficiently approaches the straight line 170.

For example, a minute value $\epsilon$ is determined in advance, and the time that the curve 140 has sufficiently approached is defined as a time that the difference between the curve 140 and the straight line 170 is below $\epsilon$. The value $\epsilon$ may be a certain value or may be set according to the absorbance at an early stage or according to the variation width of the absorbance. For example, a value obtained by multiplying the absorbance at an early stage by a constant or a value obtained by multiplying the difference between the absorbance at an early stage and the ultimate absorbance by a constant may be set as $\epsilon$. As for the sufficiently approached time, a minute value $\delta$ may be set, and the time can be defined as a time when the difference between the slopes of the curve 140 and the straight line 170 has become below $\delta$. In this case, $\delta$ may be a certain value or may be set according to the slope of the straight line 170. For example, a value obtained by multiplying the slope of the straight line 170 by a constant may be set as $\delta$.

A point 200 on the vertical axis denotes a point where the straight line 170 intersects with the vertical axis, and a point 210 on the vertical axis denotes a point where the curve 140 intersects with the vertical axis. For example, the following four types of values are calculated for the shape feature quantities.

(1) Time indicated by the point 180 on the horizontal axis 110 (Tc).

(2) Time indicated by the point 190 on the horizontal axis 110 (T1).

(3) Difference between the absorbance indicated by the point 200 on the vertical axis 120 and the absorbance indicated by the point 210 (D0).

(4) Difference between the slope of the straight line 160 and the slope of the straight line 170 (G0).

The values are obtained by numerically expressing the curve shape of the lag time section of the reaction process data in the rate method. For example, T1 is equivalent to the length of the lag time, and Tc, D0, and G0 are values indicating the magnitude of the deviation between the lag time section and the approached straight line. The values allow quantitative handling of the size of the lag time that has been sensuously observed by a person in the past.

Figure 10:
FIG. 10 is a diagram showing an example of a table describing determination formulas for determining abnormality for each type of abnormality.

Next, in step S35, the abnormality determination module 53 reads, from the storage device 12, a determination formula for determining the abnormality based on the shape feature quantities obtained in step S30. Optimal determination formulas are defined in advance using a large amount of normal and abnormal data, and for example, a table 600 in a format shown in FIG. 10 is stored in the storage device 12. A column 610 describes the types of abnormality, and a column 620 describes determination formulas for determining abnormality. In the determination formulas of the column 620, p0 to p3, q0 to q3, r0 to r3, s0 to s3, and v0 to v3 are predetermined constants. Although an example of determination by the linear determination formula using four values of Tc, T1, D0, and D1 obtained in step S35 is illustrated in the example, other shape feature quantities or the values of the parameters in the approximation formula may also be used. Since the parameter values in the approximation formula vary depending on the shape features, the parameter values can be used as the shape feature quantities. The determination formula may not be linear, and for example, the formula may be described by a logical formula.

Figure 8:
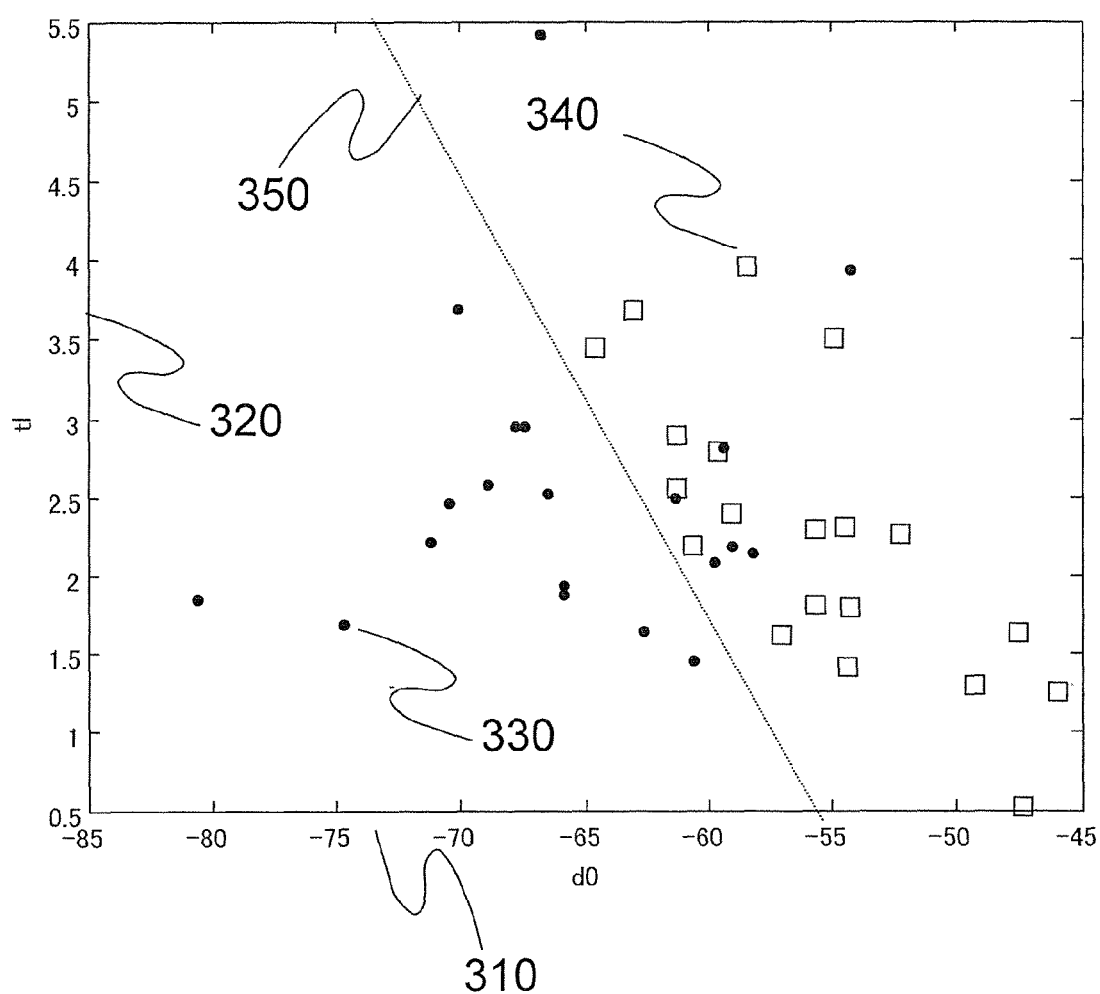
FIG. 8 is a diagram showing an example of a distribution of shape feature quantities of a reaction process curve obtained by the present invention.

Next, in step S40, the abnormality determination module 53 determines abnormality based on the determination formula selected in step S35. FIG. 8 shows a distribution of the values of T1 and D0 obtained from the reaction process data in a normal state and a distribution of T1 and D0 obtained from the reaction process data in a state in which a stir abnormality is artificially generated. A horizontal axis 310 denotes values of D0, and a vertical axis 320 denotes values of T1. Markers 330 denote a distribution of D0 and T1 obtained from the reaction process data in a normal state, and markers 340 denote a distribution of D0 and T1 obtained from the reaction process data in a stir abnormal state. For example, the stir abnormality can be detected by determining that the data positioned on the left of a straight line 350 is normal and that the data positioned on the right is abnormal. The line for determining the abnormality and normality can be obtained using a known method such as discriminant analysis.

In step S45, the abnormality determination module 53 outputs the abnormal or normal determination result determined in step S40 to the computer 10.

Although an example of using different determination formulas based on the types of abnormality to be determined has been described in steps S35 and S40, the present invention is not limited to the method. For example, the normality or the types of abnormality may be determined at once using an existing pattern recognition technique, such as a neural network, and using the shape feature quantities or the parameter values of the approximation formula. A state of not normal may be determined without specifying the type of the abnormality. In this case, a large number of approximation formula parameters and shape feature quantities are obtained in advance in the normal state, and distributions of the parameters and the quantities are obtained. In step S40, the approximation formula parameters obtained in step S25 and the shape feature quantities obtained in step S30 are compared with the distributions of the approximation formula parameters and the shape feature quantities in the normal state to determine the presence or absence of abnormality. For example, a Mahalanobis distance of the approximation formula parameters obtained in step S25, the shape feature quantities obtained in S30, and the distributions obtained in advance is calculated, and it is determined to be abnormal if the Mahalanobis distance is greater than a certain value.

Although an example, in which the control unit 13 executes the process shown in FIG. 1, has been described in the first embodiment, other sections of the analyzer may execute the process. For example, software can execute the process of FIG. 1 in the computer (PC) 10. A storage device in the computer (PC) 10 can be used as the storage device 12.

Although an example of using Expression (4) to Expression (7) as the approximation formulas has been described in the first embodiment, the approximation formulas that can be used in the present invention are not limited to Expression (4) to Expression (7). More generally, a formula can be similarly used if the formula approaches the straight line as shown in the following formula. In the formula, t denotes time, x denotes absorbance, a and b are parameters, and h (t, φ) is a function that includes a plurality of parameters φ and that approaches 0.

$$x = ax + b + h(t, \phi) \quad (8)$$

According to the first embodiment, various abnormalities, such as a stir abnormality, a dispense abnormality, and a reagent abnormality, can be highly accurately detected in each examination based on the reaction process data obtained by daily examinations or examinations using a specimen for calibration.

Second Embodiment

Next, a second embodiment of the present invention will be described in detail with reference to the drawings. As in the first embodiment, FIG. 5 shows the schematic configuration of the biochemical automated analyzer according to the second embodiment. The operations other than the operation of the control unit 13 are the same as in the first embodiment, and detailed description will not be repeated.

Figure 11:
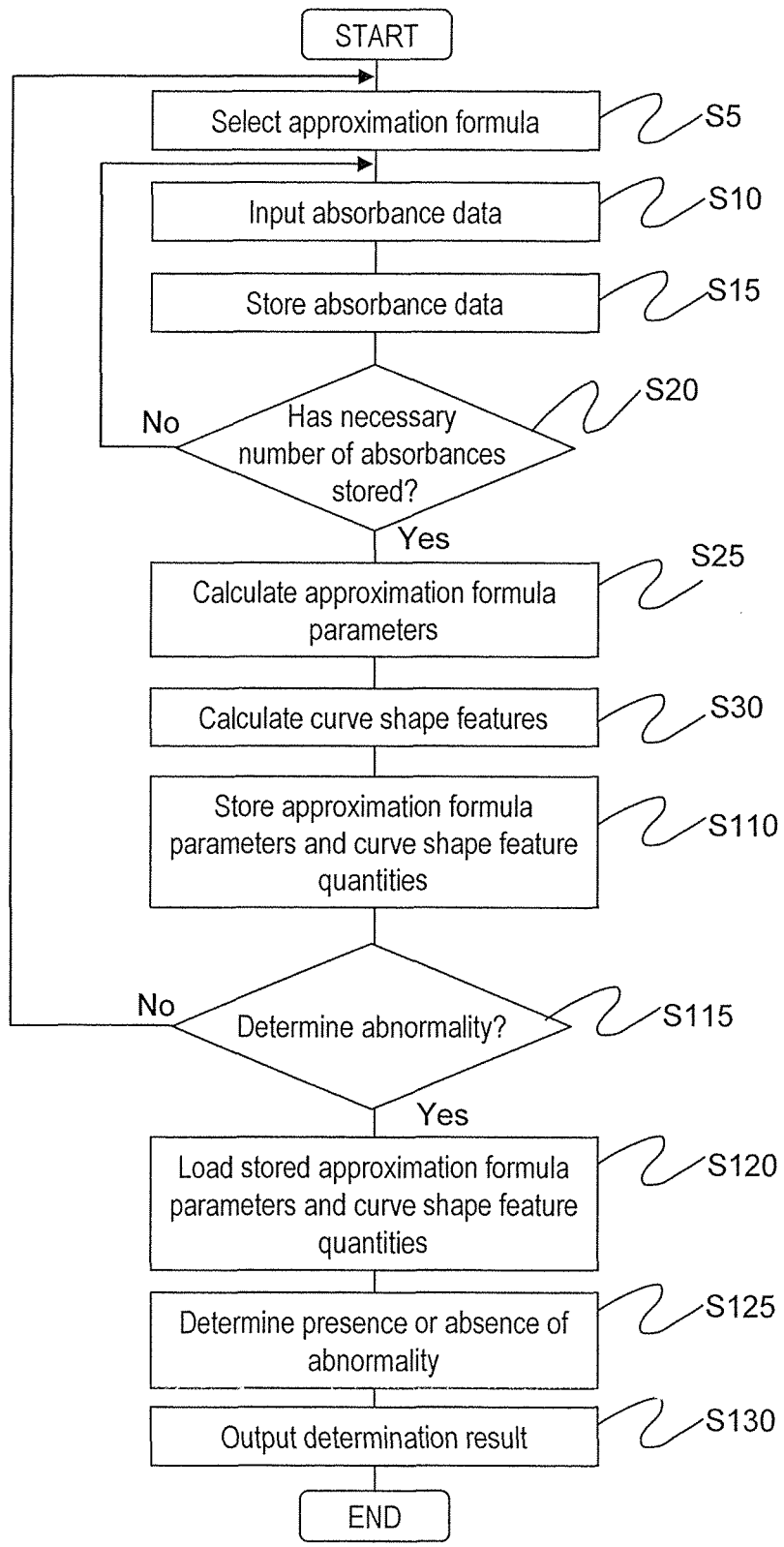
FIG. 11 is a diagram showing a processing flow of a second embodiment of the present invention.

Next, details of a process by the control unit 13 determining abnormality based on the absorbance will be described with reference to FIG. 11. FIG. 11 is a diagram showing a processing step of the section related to abnormality determination in the control unit 13. The same reference numerals are provided to the processing steps for executing the same process as the abnormality determination process by the control unit 13 in the first embodiment shown in FIG. 1. The process from step S5 to step S30 is the same as the process from step S5 to step S30 of the first embodiment shown in FIG. 1, and the description will not be repeated.

In step S110, the approximation formula parameters obtained in step S25 and the shape feature qualities obtained in step S30 are stored in the storage device 12. In step S115, the abnormality determination module 53 determines whether abnormality determination is executed. The determination of whether to execute abnormality determination in S115 may determine to execute abnormality determination, for example, every certain time. In this case, the time interval for determining abnormality is designated in advance, the elapsed time from the previous determination of abnormality is checked in step S115, and it is determined to execute abnormality determination if the elapsed time is beyond the set time interval.

The abnormality determination may be executed every time the examinations are carried out for a certain number of times. In this case, the interval of the number of times of the examinations for abnormality determination is designated in advance, the number of times of the examinations from the previous abnormality determination is checked in step S115, and it is determined to execute abnormality determination if the number of times of the examinations is beyond the set number of times.

Whether to execute abnormality determination may be determined by an instruction by the user. In this case, the abnormality determination module 53 checks whether there is an instruction for the abnormality determination from the user to the computer 10 in step S115, and it is determined to execute abnormality determination if there is an instruction.

In step S120, the approximation formula parameters and the shape feature quantities stored in the storage device 12 in step S110 are loaded to the abnormality determination module 53.

In step S120, all stored data may be loaded, or data satisfying a specific condition may be selectively loaded. When the data is selectively loaded, for example, only data of a specific examination item or data of a specific examination item in which a value of an examination result is within a specific range may be loaded. Only data of the calibrator or the quality control sample may be loaded. The abnormality can be more highly accurately detected by selectively using only the data in a specific condition.

In step S125, the abnormality determination module 53 determines abnormality based on the approximation formula parameters and the shape feature quantities loaded in step S120. For example, the abnormality determination module 53 obtains the distributions of the approximation formula parameters and the shape feature quantities loaded in step S120, checks whether the shapes of the distributions are different from the distributions of the approximation formula parameters and the shape feature quantities measured and obtained in a normal state, and determines that there is an abnormality if the distributions are different. A technique, such as existing statistical testing, can be used to determine whether the shapes of the distributions are different. In this way, an abnormality of an analyzer or a reagent that is hard to figure out in the determination of abnormality based on single data can be determined using a plurality of data (approximation formula parameters and shape feature quantities).

In step S130, the determination result in step S125 is output from the abnormality determination module 53 to the computer 10.

According to the second embodiment, various changes of the stirring mechanism, the dispense mechanism, the reagent performance, and the like can be highly accurately detected from the reaction process data obtained from daily examinations or examinations using the calibrator or the quality control sample. While the determination is made using single data (approximation formula parameters, shape feature quantities) in the first embodiment, the determination is made using a plurality of data in the second embodiment. Therefore, an abnormal state that is hard to determine from single data can also be detected.

Although an example in which the control unit 13 executes the process shown in FIG. 11 has been described in the second embodiment, other sections of the analyzer can also execute the process. For example, software in the computer (PC) 10 can execute the process of FIG. 11. The storage device inside the computer (PC) 10 can also be used as the storage device 12.

Third Embodiment

Next, a third embodiment of the present invention will be described in detail with reference to the drawings. The schematic configuration of the biochemical automated analyzer according to the third embodiment is also shown in FIG. 5 as in the first embodiment. The operations other than the operation of the control unit 13 are the same as in the first embodiment, and the detailed description will not be repeated.

Figure 12:
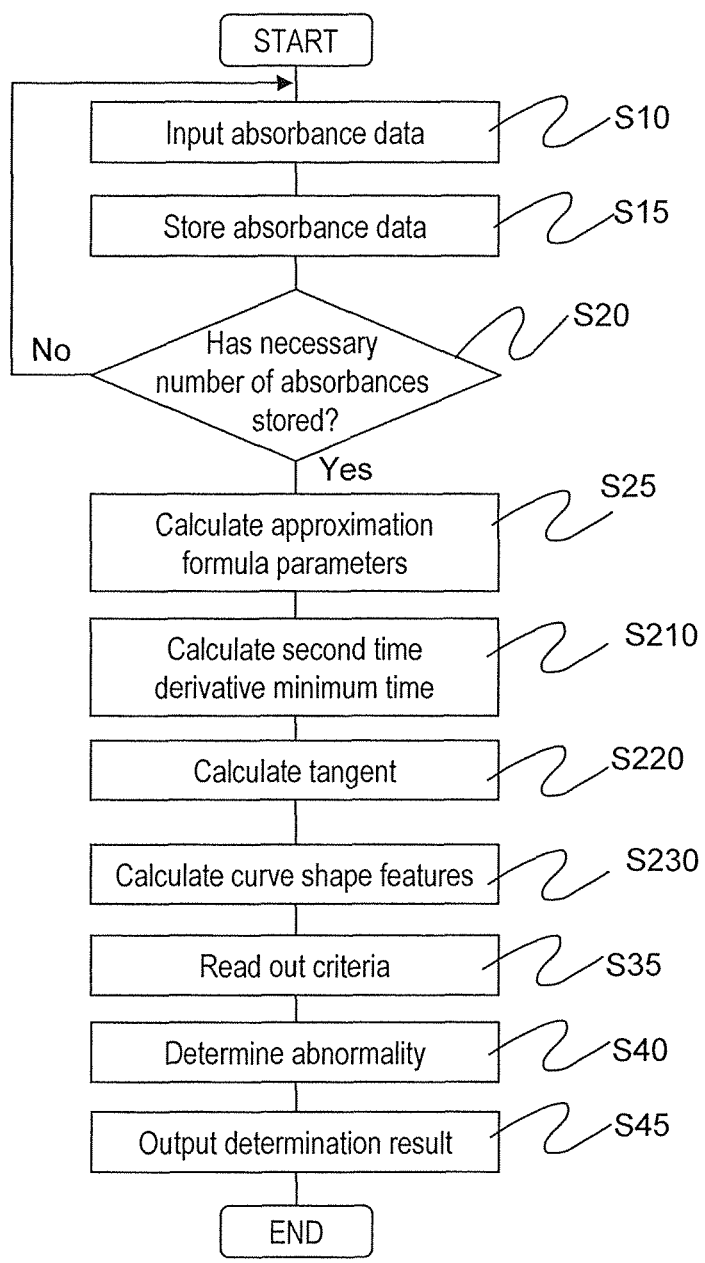
FIG. 12 is a diagram showing a processing flow of a third embodiment of the present invention.

Next, details of a process by the control unit 13 determining abnormality based on the absorbance will be described with reference to FIG. 12. FIG. 12 is a diagram showing a processing step of the section related to the determination of abnormality in the control unit 13. The same reference numerals are provided to the processing steps for executing the same process as the abnormality determination process by the control unit 13 in the first embodiment shown in FIG. 1.

Although the functions for approaching the straight line are used as the formulas for approximating the reaction process data in the first embodiment, the functions used for the approximation are not particularly limited in the present embodiment. Here, the function used for the approximation is expressed by Expression (9). In the formula, t denotes time, x denotes absorbance, and φ denotes a plurality of parameters.

$$x=f(t,\phi) \quad (9)$$

For example, φ denotes a0, a1, and a2 when a quadratic function of t is used for f (t, φ) as shown in Expression (10).

$$f(t,\phi)=a0+a1*t+a2*t*t \quad (10)$$

The process from steps S10 to S25 is the same as the process in the first embodiment shown in FIG. 1, and the detailed description will not be repeated. In step S210, the approximation calculation module 52 calculates a time Tv that minimizes (preferably 0) the absolute value of the second time derivative of the formula (hereinafter, "approximation formula") in which the approximation parameters obtained in step S25 are assigned to Expression (9). In the formula, the start time of the reaction is time 0. In step S220, a tangent of Expression (9) at the time Tv is calculated.

Figure 13:
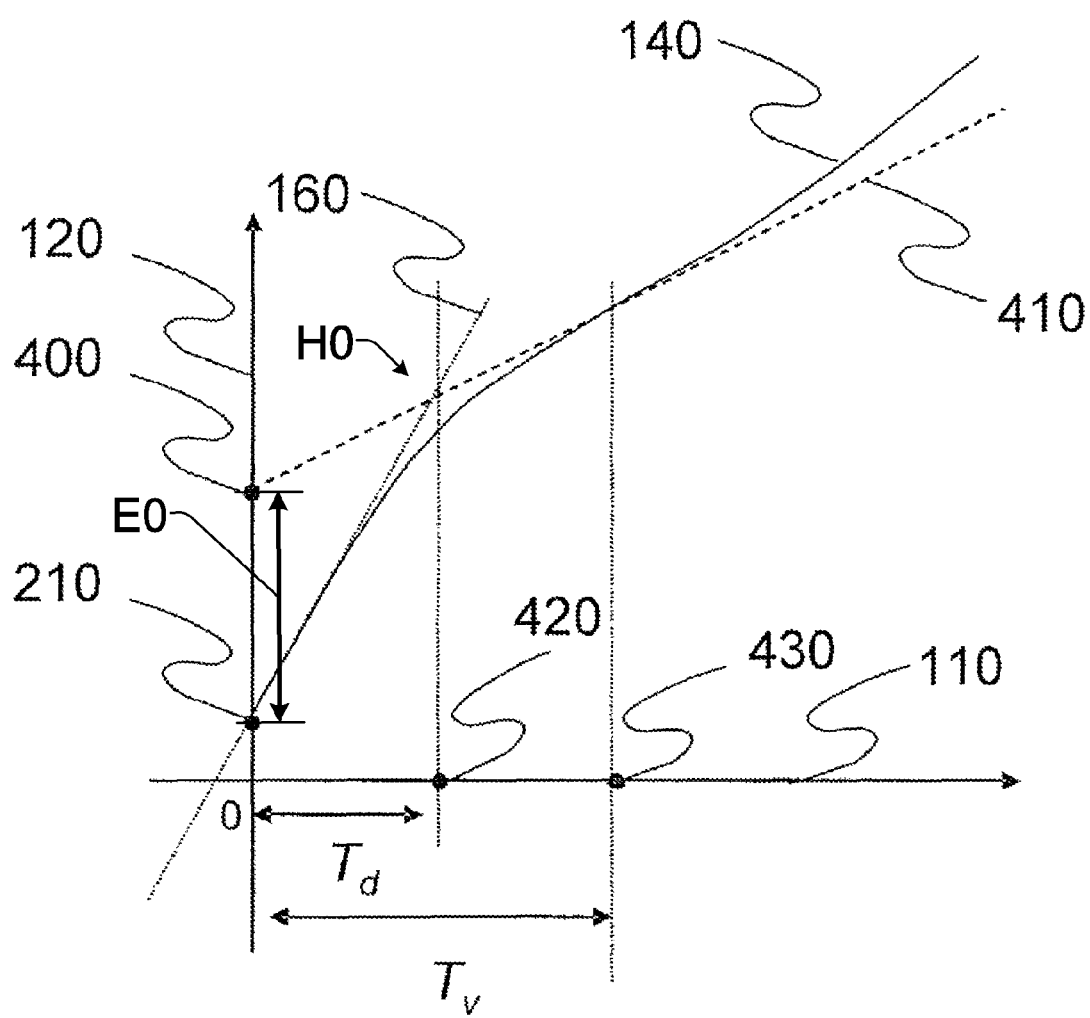
FIG. 13 is a diagram explaining a method of numerically expressing shape features of a curve section at an early stage of reaction.

Next, in step S230, the approximation calculation module 52 calculates numeric values (shape feature quantities) indicating the features of the absorbance change pattern of the section where the absorbance at an early stage of the reaction changes in a curved manner. An example of the shape feature quantities will be described with reference to FIG. 13. In FIG. 13, the horizontal axis 110 denotes a lapse of time from the start of the reaction, and the vertical axis 120 denotes absorbance. The curve 140 denotes an approximated curve of the absorbance change calculated by the approximation formula. The straight line 160 denotes a tangent of the curve 140 at the start of the reaction, and a straight line 410 denotes a tangent at the time tv obtained in step S220. A point 420 on the horizontal axis 110 denotes time that the straight line 160 and the tangent 410 intersect. A point 430 on the horizontal axis 110 denotes the time Tv calculated in step S210. A point 400 on the vertical axis denotes a point where the tangent 410 intersects with the vertical axis, and the point 210 on the vertical axis denotes a point where the curve 140 intersects with the vertical axis. For example, the following four types of values are calculated and used as the shape feature quantities.

(1) Time indicated by the point 420 on the horizontal axis 110 (Td)

(2) Time indicated by the point 430 on the horizontal axis 110 (Tv)

(3) Difference between the absorbance indicated by the point 400 on the vertical axis 120 and the absorbance indicated by the point 210 (E0)

(4) Difference between the slope of the straight line 160 and the slope of the tangent 410 (H0).

The values are numerical expressions of the curve shape of the lag time section of the reaction process data in the rate method. For example, Tv is equivalent to the length of the lag time, and Td, E0, and H0 are values indicating the sizes of the deviation between the lag time section and the approaching straight line. The values allow quantitative handling of the size of the lag time that has been sensuously observed by a person in the past.

Steps S35, S40, and S45 are the same process as steps S35, S40, and S45 in the first embodiment if the shape feature quantities Tc, TL, D0, and G0 in the first embodiment are replaced by the shape feature quantities Td, Tv, E0, and H0 in the present embodiment. Therefore, the description will not be repeated.

The reaction process data obtained in the measurement by the rate method may change again in a curved manner after a linear change with a lapse of time. The present embodiment allows obtaining a preferable result even in such a case.

Although an example in which the control unit 13 executes the process shown in FIG. 12 has been described in the third embodiment, other sections of the analyzer also can execute the process. For example, software in the computer (PC) 10 can execute the process of FIG. 12.

INDUSTRIAL APPLICABILITY

As described in the first to third embodiments, the automated analyzer to which the present invention is applied can check abnormalities of analyzers, reagents, and the like from daily examination data and can contribute to the maintenance of the performance of the analyzers.

REFERENCE SIGNS LIST

1: sample disc, 2: reagent disc, 3: reaction disc, 4: reaction vessel, 5: sampling mechanism, 6: pipetting mechanism, 7: stirring mechanism, 8: photometry mechanism, 9: washing mechanism, 10: computer (PC), 12: storage device, 13: control unit, 14: piezoelectric element driver 15: stirring mechanism controller, 16: sample container, 17: circular disc, 18: reagent bottle, 19: circular disc, 20: cooling box, 21: reaction container, 22: reaction container holder, 23: drive mechanism, 24: probe, 25: support shaft, 26: arm, 27: probe, 28: support shaft, 29: arm, 31: fixation unit, 33: nozzle, 34: vertical drive mechanism, 51: input/ output module, 52: approximation calculation module, 53: abnormality determination module, 54: storage device, 55: data bus, 110: axis indicating lapse of time, 120: axis indicating absorbance, 130: markers indicating absorbance measured at each time, 140: curve indicating absorbance calculated by approximation formula, 150: curve schematically showing absorbance change by rate method, 160: tangent at start of reaction of curve in which reaction process data is approximated, 170: straight line approached by curve in which reaction process data is approximated, 180: point indicating time when straight line 160 and straight line 170 intersect, 190: point indicating time when curve 140, in which reaction process data is approximated, sufficiently approaches straight line 170, 200: point where straight line 170 intersects with vertical axis 120, 210: point where curve 140 intersects with vertical axis 120, 310: axis indicating value of D0, 320: axis indicating value of T1, 330: markers indicating distributions of D0 and T1 obtained from reaction process data in normal state, 340: markers indicating distributions of D0 and T1 obtained from reaction process data in stir abnormal state, 350: borderline for identifying normality and stir abnormality, 400: point where tangent 410 intersects with vertical axis, 410: tangent of curve 140 at time Tv when second time derivative of curve 140, in which reaction process data is approximated, is minimum, 420: point indicating time when straight line 160 and tangent 410 intersect, 430: point indicating time Tv when second time derivative of curve 140, in which reaction process data is approximated, is minimum, 500: table describing optimal approximation formulas for combinations of examination items and reagents to be used, 510: column describing examination items, 520: column describing types of reagents, 530: column describing types of approximation formulas, 600: table describing determination methods by type of detected abnormality, 610: column describing types of detected abnormality, 620: column describing determination methods

The invention claimed is:

1. An automated analyzer comprising:
a reaction container;
first dispense means for dispensing a sample of an examination item to the reaction container;
second dispense means for dispensing a reagent to be reacted with the sample dispensed to the reaction container;
a stirrer for mixing the sample and the reagent in the reaction container;
a photometer configured to detect one or more measurements of a reaction process of the sample and the reagent in the reaction container;
a storage that stores a determination formula and a distribution of approximation formula parameters and shape feature quantities obtained in advance for a normal state and a plurality of approximation formulas in association with at least one of reagent information or examination item information, the approximation formulas including Expression (4) to Expression (7) as follows:

$$x = a^*t + b + c^*\exp(-k^*t) \quad (4)$$

$$x = a^*t + b + e/(t+d) \quad (5)$$

$$x = a^*t + b + w/\{\exp(u^*t) + v\} \quad (6)$$

$$x = a^*t + b + p^*\log\{1 + q^*\exp(r^*t)\} \quad (7);$$

wherein t denotes time, x denotes absorbance, and each of a, b, c, d, e, k, p, q, r, u, v, and w are parameters; and
a control unit configured to:
acquire, from the photometer, a plurality of measurement point data of the reaction process
select, based on a combination of the reagent and the examination item, one of the plurality of approximation formulas stored in the storage to approximate the plurality of measurement point data;
store the plurality of measurement point data to obtain a threshold number of measurement point data;
determine the parameters of the selected approximation formula for minimizing a difference between a time change of an absorbance expressed by the selected approximation formula and a time change of an actual absorbance;
determine, based on the selected approximation formula, an approximated curve that approximates the plurality of measurement point data;
determine at least one shape feature quantity (1) to (4) from the approximated curve as an index, wherein a tangent of the approximated curve at a start of the reaction process is a first straight line, and a straight line that approaches the approximated curve is a second straight line, the shape feature quantities (1) to (4) including:
(1) a time when the first and second straight lines intersect,
(2) a time when the second straight line approaches below a predetermined threshold,
(3) a difference between values of the first and second straight lines at a reaction start time,
(4) a difference between slopes of the first and second straight lines;
determine an abnormal measurement based at least on the index obtained from the approximated curve and at least one of:
the determination formula defined in advance for a type of abnormality based on prior normal and abnormal data; or
the distribution of approximation formula parameters and shape feature quantities obtained in advance for a normal state; and
in response to determining the abnormal measurement, output a result including an indication of the abnormal measurement.

2. The automated analyzer according to claim 1, wherein the control unit is further configured to:
calculate the parameters of the selected approximation formula to reduce a square error between the measurement data and the approximated curve to set the index.

3. The automated analyzer according to claim 1, wherein the control unit is further configured to:
determine the abnormal measurement at preset time intervals from a start of the reaction.

4. The automated analyzer according to claim 1, wherein the control unit is further configured to determine the abnormal measurement by comparing a distribution of the index determined based on all of the plurality of measurement point data with an index determined based on single measurement point data read out from among the plurality of measurement data.

5. The automated analyzer according to claim 1, wherein the control unit is further configured to:

obtain the second straight line as a tangent at a time when an absolute value of a second time derivative of the approximated curve is minimum; and use the tangent to calculate the index of the approximated curve for determining the abnormal measurement based on the index.

6. The automated analyzer according to claim 5, wherein the plurality of approximation formulas stored in the storage further include an expression for time-series data of measurement values measured with a lapse of time as follows:

$$x = ax + b + h(t, \phi)$$

in which t denotes time when the measurement value is measured, x denotes the absorbance, a and b denote parameters, and h (t, φ) denotes a function that includes a plurality of parameters φ and that approaches 0, and the parameters a, b, and φ are set as the index to determine abnormality.

7. The automated analyzer according to claim 1, wherein the photometer is configured to detect light transmitted through the reaction container to provide an indication of the absorbance to the control unit as one or more of the measurement point data.

8. The automated analyzer according to claim 1, wherein the control unit is further configured to output the result to a computer in communication with the automated analyzer to cause a notification to be provided to a user.

9. The automated analyzer according to claim 1, wherein the abnormal measurement is related to stirring, and the control unit is further configured to include an indication of a problem with the stirrer with the output result.

10. The automated analyzer according to claim 1, wherein the abnormal measurement is related to degradation of the reagent, and the control unit is further configured to include an indication of a problem with the reagent with the output result.

11. The automated analyzer according to claim 1, wherein the abnormal measurement is related to dispensing, and the control unit is further configured to include an indication of a problem with at least one of the first or second dispense means with the output result.

12. An automated analyzer comprising:
    a reaction container;
    first dispense means for dispensing a sample of an examination item to the reaction container;
    second dispense means for dispensing a reagent to be reacted with the sample dispensed to the reaction container;
    a stirrer for mixing the sample and the reagent in the reaction container;
    a photometer configured to detect one or more measurements of a reaction process of the sample and the reagent in the reaction container;
    a storage that stores a determination formula and a distribution of approximation formula parameters and shape feature quantities obtained in advance for a normal state and a plurality of approximation formulas in association with at least one of reagent information or examination item information, the approximation formulas including Expression (4) to Expression (7) as follows:

$$x = a^*t + b + c^* \exp(-k^*t) \quad (4)$$

$$x = a^*t + b + e/(t+d) \quad (5)$$

$$x = a^*t + b + w/\{\exp(u^*t) + v\} \quad (6)$$

$$x = a^*t + b + p^* \log\{1 + q^* \exp(r^*t)\} \quad (7);$$

wherein t denotes time, x denotes absorbance, and each of a, b, c, d, e, k, p, q, r, u, v, and w are parameters; and a computer configured to:
    acquire, from the photometer, a plurality of measurement point data of the reaction process;
    select, based on a combination of the reagent and the examination item, one of the plurality of approximation formulas stored in the storage to approximate the plurality of measurement point data;
    store the plurality of measurement point data to obtain a threshold number of measurement point data;
    determine the parameters of the selected approximation formula for minimizing a difference between a time change of an absorbance expressed by the selected approximation formula and a time change of an actual absorbance;
    determine, based on the selected approximation formula, an approximated curve that approximates the plurality of measurement point data;
    determine at least one shape feature quantity (1) to (4) from the approximated curve as an index, wherein a tangent of the approximated curve at a start of the reaction process is a first straight line, and a straight line that approaches the approximated curve is a second straight line, the shape feature quantities (1) to (4) including:
        (1) a time when the first and second straight lines intersect,
        (2) a time when the second straight line approaches below a predetermined threshold,
        (3) a difference between values of the first and second straight lines at a reaction start time,
        (4) a difference between slopes of the first and second straight lines;
    determine an abnormal measurement based at least on the index obtained from the approximated curve and at least one of:
        the determination formula defined in advance for a type of abnormality based on prior normal and abnormal data; or
        the distribution of approximation formula parameters and shape feature quantities obtained in advance for a normal state; and
    in response to determining the abnormal measurement, output a result including an indication of the abnormal measurement.

13. The automated analyzer according to claim 12, wherein the computer is further configured to:
    calculate the parameters of the selected approximation formula to reduce a square error between the measurement data and the approximated curve to set the index.

14. The automated analyzer according to claim 12, wherein the computer is further configured to:
    determine the abnormal measurement at preset time intervals from a start of the reaction.

15. The automated analyzer according to claim 12, wherein the abnormal measurement is related to stirring, and the computer is further configured to include an indication of a problem with the stirrer with the output result.

16. The automated analyzer according to claim 12, wherein the abnormal measurement is related to degradation of the reagent, and the computer is further configured to include an indication of a problem with the reagent with the output result.

17. The automated analyzer according to claim 12, wherein the abnormal measurement is related to dispensing, and the computer is further configured to include an indication of a problem with at least one of the first or second dispense means with the output result.

18. The automated analyzer according to claim 12, wherein the computer is further configured to:
provide, in addition to the indication of the abnormal measurement, optimal parameters associated with at least one of the examination item or the reagent.

\* \* \* \* \*